(12) United States Patent
Hart et al.

(10) Patent No.: US 10,832,653 B1
(45) Date of Patent: Nov. 10, 2020

(54) PROVIDING CONTENT ON MULTIPLE DEVICES

(71) Applicant: Amazon Technologies, Inc., Seattle, WA (US)

(72) Inventors: Gregory Michael Hart, Mercer Island, WA (US); Jeffrey P. Bezos, Greater Seattle, WA (US)

(73) Assignee: Amazon Technologies, Inc., Seattle, WA (US)

( * ) Notice: Subject to any disclaimer, the term of this patent is extended or adjusted under 35 U.S.C. 154(b) by 0 days.

(21) Appl. No.: 16/180,330

(22) Filed: Nov. 5, 2018

Related U.S. Application Data

(63) Continuation of application No. 15/792,304, filed on Oct. 24, 2017, now Pat. No. 10,121,465, which is a
(Continued)

(51) Int. Cl.
  *G10L 13/00*  (2006.01)
  *G10L 15/00*  (2013.01)
  (Continued)

(52) U.S. Cl.
  CPC ............... *G10L 15/00* (2013.01); *G10L 15/22* (2013.01); *G10L 13/00* (2013.01); *G10L 21/06* (2013.01); *G10L 2015/223* (2013.01)

(58) Field of Classification Search
  CPC .......... G10L 15/22; G10L 21/06; G10L 15/00
  See application file for complete search history.

(56) References Cited

U.S. PATENT DOCUMENTS

| | | | |
|---|---|---|---|
| 6,721,705 | B2 | 4/2004 | Kurganov et al. |
| 7,418,392 | B1 | 8/2008 | Mozer et al. |
(Continued)

FOREIGN PATENT DOCUMENTS

| | | |
|---|---|---|
| CN | 102006373 | 4/2011 |
| CN | 201830294 | 5/2011 |
(Continued)

OTHER PUBLICATIONS

Chinese Office Action dated Jun. 4, 2018 for Chinese patent application No. 201480015194.0, a counterpart foreign appliation of U.S. Appl. No. 13/829,156, 11 pgs.
(Continued)

*Primary Examiner* — Daniel C Washburn
*Assistant Examiner* — Oluwadamilola M Ogunbiyi
(74) *Attorney, Agent, or Firm* — Lee & Hayes, P.C.

(57) ABSTRACT

Techniques for receiving a voice command from a user and, in response, providing audible content to the user via a first device and providing visual content for the user via a second device. In some instances, the first device includes a microphone for generating audio signals that include user speech, as well as a speaker for outputting audible content in response to identified voice commands from the speech. However, the first device might not include a display for displaying graphical content. As such, the first device may be configured to identify devices that include displays and that are proximate to the first device. The first device may then instruct one or more of these other devices to output visual content associated with a user's voice command.

20 Claims, 10 Drawing Sheets

Related U.S. Application Data continuation of application No. 13/872,991, filed on Apr. 29, 2013, now Pat. No. 9,842,584.

(60) Provisional application No. 61/785,662, filed on Mar. 14, 2013.

(51) Int. Cl.
*G10L 15/22* (2006.01)
*G10L 21/06* (2013.01)

(56) References Cited

U.S. PATENT DOCUMENTS

| | | | |
|---|---|---|---|
| 7,516,192 | B2 | 4/2009 | Brown |
| 7,672,931 | B2 | 3/2010 | Hurst-Hiller et al. |
| 7,698,131 | B2 | 4/2010 | Bennett |
| 7,720,683 | B1 | 5/2010 | Vermeulen et al. |
| 7,774,204 | B2 | 8/2010 | Mozer et al. |
| 8,249,876 | B1 | 8/2012 | Ainslie |
| 8,296,383 | B2 | 10/2012 | Lindahl |
| 8,315,360 | B2 | 11/2012 | Bushey et al. |
| 8,326,829 | B2 | 12/2012 | Gupta |
| 8,369,799 | B2 | 2/2013 | Taylor |
| 8,370,762 | B2 | 2/2013 | Abbott |
| 8,434,153 | B2 | 4/2013 | Sundaramurthy et al. |
| 8,676,273 | B1 * | 3/2014 | Fujisaki ............ H04M 1/6505 455/567 |
| 8,713,614 | B2 | 4/2014 | Dodd |
| 8,793,305 | B2 | 7/2014 | Fiatal |
| 8,930,492 | B2 | 1/2015 | Brown et al. |
| 9,438,949 | B2 | 9/2016 | Davis et al. |
| 2003/0139933 | A1 | 7/2003 | Kimmel |
| 2004/0260438 | A1 | 12/2004 | Chernetsky et al. |
| 2005/0027539 | A1 | 2/2005 | Weber et al. |
| 2005/0172319 | A1 * | 8/2005 | Reichardt ............ H04N 5/765 725/52 |
| 2005/0232283 | A1 * | 10/2005 | Moyer ............ H04L 12/2803 370/401 |
| 2006/0023063 | A1 | 2/2006 | Okawa |
| 2006/0142005 | A1 * | 6/2006 | Takaluoma ............ G06F 9/542 455/435.1 |
| 2007/0011133 | A1 | 1/2007 | Chang |
| 2007/0061149 | A1 | 3/2007 | Chang |
| 2007/0174350 | A1 * | 7/2007 | Pell ............ G06F 3/038 |
| 2008/0077387 | A1 * | 3/2008 | Ariu ............ G10L 15/22 704/3 |
| 2008/0180519 | A1 | 7/2008 | Cok |
| 2008/0243513 | A1 | 10/2008 | Bucchieri et al. |
| 2009/0204409 | A1 | 8/2009 | Mozer et al. |
| 2009/0204410 | A1 | 8/2009 | Mozer et al. |
| 2010/0036660 | A1 | 2/2010 | Bennett |
| 2010/0088100 | A1 | 4/2010 | Lindahl |
| 2010/0174801 | A1 | 7/2010 | Tabaaloute |
| 2010/0241963 | A1 * | 9/2010 | Kulis ............ G06F 3/167 715/727 |
| 2010/0280641 | A1 * | 11/2010 | Harkness ......... H04N 21/25891 700/94 |
| 2011/0006971 | A1 | 1/2011 | Ebey et al. |
| 2011/0029315 | A1 | 2/2011 | Nichols et al. |
| 2011/0063506 | A1 | 3/2011 | Reams |
| 2011/0099157 | A1 | 4/2011 | LeBeau et al. |
| 2011/0145874 | A1 * | 6/2011 | Bi ............ H04N 21/478 725/110 |
| 2011/0313775 | A1 | 12/2011 | Laligand et al. |
| 2012/0173238 | A1 * | 7/2012 | Mickelsen ............ G10L 15/30 704/246 |
| 2012/0223885 | A1 | 9/2012 | Perez |
| 2012/0232906 | A1 | 9/2012 | Lindahl |
| 2012/0245945 | A1 | 9/2012 | Miyauchi et al. |
| 2012/0253814 | A1 * | 10/2012 | Wang ............ G06F 16/9577 704/260 |
| 2012/0259707 | A1 | 10/2012 | Thielke et al. |
| 2012/0331548 | A1 | 12/2012 | Tseng et al. |
| 2013/0007289 | A1 * | 1/2013 | Seo ............ G06F 8/654 709/227 |
| 2013/0125168 | A1 | 5/2013 | Agnihotri et al. |
| 2013/0132081 | A1 * | 5/2013 | Ryu ............ G10L 21/06 704/235 |
| 2013/0273960 | A1 | 10/2013 | Zhang et al. |
| 2013/0325451 | A1 | 12/2013 | Levien et al. |
| 2013/0339026 | A1 | 12/2013 | Lee |
| 2014/0016036 | A1 | 1/2014 | Takahashi et al. |
| 2014/0111415 | A1 * | 4/2014 | Gargi ............ G06F 3/017 345/156 |
| 2014/0136195 | A1 | 5/2014 | Abdossalami et al. |
| 2014/0143666 | A1 | 5/2014 | Kennedy et al. |
| 2014/0146644 | A1 | 5/2014 | Chen |
| 2014/0177630 | A1 | 6/2014 | Wang et al. |
| 2014/0278438 | A1 | 9/2014 | Hart et al. |
| 2014/0364166 | A1 | 12/2014 | Tang et al. |
| 2015/0148929 | A1 * | 5/2015 | Weiss ............ G06Q 30/02 700/94 |
| 2015/0229685 | A1 | 8/2015 | Brebion et al. |
| 2017/0135543 | A1 * | 5/2017 | Halloran ............ A47L 9/009 |

FOREIGN PATENT DOCUMENTS

| | | |
|---|---|---|
| JP | S63047823 | 2/1988 |
| JP | H09265300 | 10/1997 |
| JP | H11109989 | 4/1999 |
| JP | 2003108174 | 4/2003 |
| JP | 2007299159 | 11/2007 |
| JP | 2009025538 | 2/2009 |
| WO | WO2011088053 A2 | 7/2011 |
| WO | WO2014100933 | 7/2014 |

OTHER PUBLICATIONS

Chinese Office Action dated Jul. 4, 2017 for Chinese patent application No. 201480015194.0, a counterpart foreign application of U.S. Appl. No. 13/829,156, 15 pgs.

Extended European Search Report dated Oct. 28, 2016 for European patent application No. 14775220.8, 7 pages.

Translated Japanese Office Action dated Jan. 1, 2016 for Japanese Patent Application No. 2016-502105, a counterpart foreign application of U.S. Appl. No. 13/829,156, 4 pages.

Office Action for U.S. Appl. No. 13/829,156, dated Jan. 15, 2015, Gregory Michael Hart, "Providing Content on Multiple Devices", 16 pages.

Office Action for U.S. Appl. No. 13/829,156, dated Aug. 10, 2017, Gregory, "Providing Content on Multiple Devices" 30 pages.

Office Action for U.S. Appl. No. 13/872,991, dated Dec. 4, 2014, Gregory Michael Hart, "Providing Content On Multiple Devices", 23 pages.

Office Action for U.S. Appl. No. 15/792,304, dated Dec. 14, 2017, Hart, "Providing Content on Multiple Devices", 22 pages.

Office Action for U.S. Appl. No. 13/829,156, dated Feb. 16, 2018, Hart, "Providing Content on Multiple Devices", 28 pages.

Office action for U.S. Appl. No. 13/829,156, dated Feb. 8, 2017, Hart et al, "Providing Content on Multiple Devices", 28 pages.

Office action for U.S. Appl. No. 13/872,991, dated Mar. 16, 2016, Hart et al., "Providing Content On Multiple Devices", 22 pages.

Office action for U.S. Appl. No. 13/829,156, dated Mar. 18, 2016, Hart et al., "Providing Content on Multiple Devices", 23 pages.

Office action for U.S. Appl. No. 13/872,991, dated Jul. 2, 2015, Hart et al., "Providing Content On Multiple Devices", 24 pages.

Office action for U.S. Appl. No. 13/829,156, dated Sep. 15, 2016, Hart et al, "Providing Content on Multiple Devices", 25 pages.

Final Office action for U.S. Appl. No. 13/829,156, dated Sep. 17, 2015, Hart et al., "Providing Content on Multiple Devices", 20 pages.

PCT Search Report and Written Opinion dated Aug. 11, 2014 for PCT Application No. PCT/US14/26326, 8 Pages.

Pinhanez, "The Everywhere Displays Projector: A Device to Create Ubiquitous Graphical Interfaces", IBM Thomas Watson Research Center, Ubicomp 2001, Sep. 30-Oct. 2, 2001, 18 pages.

(56) References Cited

OTHER PUBLICATIONS

European Office Action dated Mar. 13, 2019 for European Patent Application No. 14775220.8, a counterpart foreign application of U.S. Pat. No. 10,133,546, 5 pages.
European Office Action dated Oct. 29, 2019 for European Patent Application No. 14775220.8, a counterpart of U.S. Pat. No. 10,133,546, 5 pages.

* cited by examiner

PROVIDING CONTENT ON MULTIPLE DEVICES

CROSS REFERENCE TO RELATED PATENT APPLICATIONS

This application is a continuation of and claims priority to commonly assigned, co-pending, U.S. patent application Ser. No. 15/792,304, filed Oct. 24, 2017, which claims priority to U.S. patent application Ser. No. 13/872,991, filed Apr. 29, 2013, Now U.S. Pat. No. 9,842,584, Issued Dec. 12, 2017, which claims priority to the Provisional Application Ser. No. 61/785,662, filed on Mar. 14, 2013, entitled "Providing Content on Multiple Devices". Application Ser. Nos. 15/792,304, 13/872,991 and 61/785,662 are fully incorporated herein by reference.

BACKGROUND

Homes are becoming more wired and connected with the proliferation of computing devices such as desktops, tablets, entertainment systems, and portable communication devices. As computing devices evolve, many different ways have been introduced to allow users to interact with these devices, such as through mechanical means (e.g., keyboards, mice, etc.), touch screens, motion, and gesture. Another way to interact with computing devices is through a user speaking to a device and the device outputting audio to the user in return. However, in some instances, certain content is best output in a form other than audio alone.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different figures indicates similar or identical components or features.

DETAILED DESCRIPTION

Figure 1:
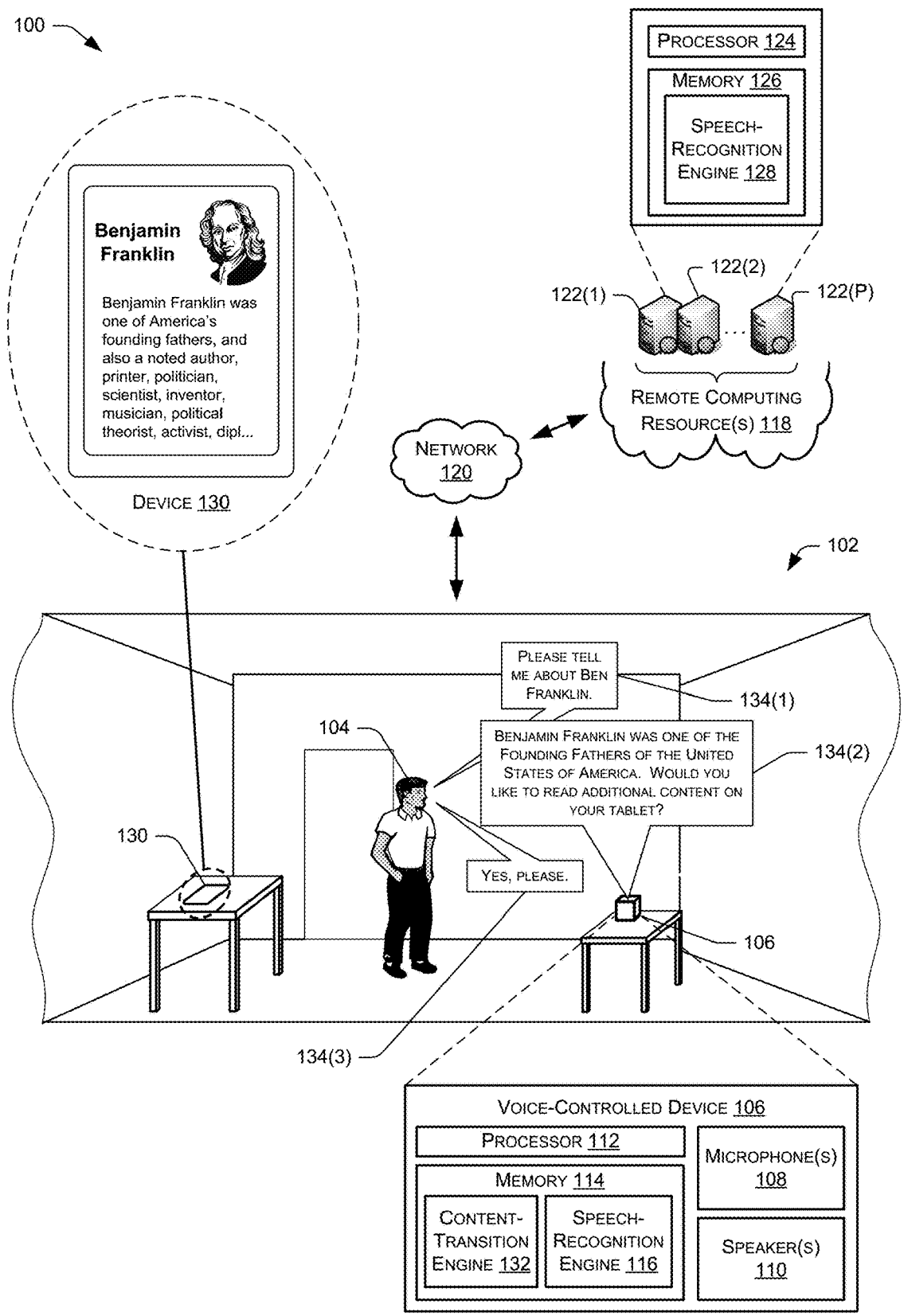
FIG. 1 shows an illustrative voice interaction computing architecture set in a home environment, according to various implementations.

This disclosure describes techniques for receiving a voice command from a user and, in response, providing audible content to the user using a first device and providing visual content for the user using a second device. In some instances, the first device includes a microphone for generating audio signals representative of user speech, as well as a speaker for outputting audible content in response to identified voice commands in the user speech. However, the first device might not include a display for displaying graphical content. As such, the first device may be configured to identify devices that include displays and that are proximate to the first device. The first device may then instruct one or more of these other devices to output visual content associated with a user's voice command.

For example, envision that a user provides the following voice command to the first device, which decodes the voice command: "Who was Benjamin Franklin?" In response, the first device may obtain content about Benjamin Franklin, such as a summary of Benjamin Franklin's most famous accomplishments. In addition, the first device or another intermediary device may instruct a second, proximate device to display additional content regarding Benjamin Franklin, such as a web page that specifies additional details about the life of Benjamin Franklin. The first device may provide this instruction in response to the user's initial voice command, or in response to the user issuing a subsequent voice command (e.g., "Please move this content to my tablet"). In one example, the first device may identify one or more devices that include display capabilities, are associated with the user issuing the voice command, and are within a same environment as the first device and the user. For instance, the first device may instruct a phone of the user, a tablet or laptop of the user, a desktop computer of the user, an electronic book reader device of the user, or any other client computing device of the user to display the visual content regarding Benjamin Franklin.

In some instances, the first device provides information including this instruction automatically upon the user issuing the voice command. For instance, the first device may simply provide information to the user's tablet computing device instructing it to display the details regarding Benjamin Franklin before, after, or while the first device outputs the audible content. In other instances, the device may provide information including the instruction in response to receiving an additional voice command from the user. For example, after finishing outputting a summary of Benjamin Franklin, the first device may audibly output the following query: "Would you like to see additional content on your tablet?" If the user responds positively, then the device may provide information to the second device instructing the second device to display additional content. In some implementations, the information may include instructions, the additional content, a location identifier or link identifying a location from which the additional content can be obtained, and/or any combination thereof. In another example, the user may simply issue the request, either before, while, or after the first device outputs the audible content. For instance, the user may state the following: "Please move this content to my tablet."

In addition, the second device may display content in any number of ways. In some implementations, the second device may include an application that is specifically configured to interact with the first device (e.g., a "companion application"). The companion application may be configured to receive information and/or instructions from the first device and/or a remote computing resource and display the appropriate content associated with the user's command. For instance, the application may display one or more links that lead to web sites, applications, or other destinations that include content about Benjamin Franklin. Additionally or alternatively, the application may directly pull in and display this content, such as detailed information about Benjamin Franklin.

In some instances, the application may also display one or more interpretations of the voice command as decoded by the first device or another device. By doing so, the user may correct the voice command, which may aid in training a speech recognition model for use in performing speech recognition on subsequent audio signals that include speech from the user. The user may also choose to verify that the voice command was interpreted correctly. In instances where the application displays one or more interpretations of the voice command, the application may also display respective search results associated with each interpretation. The search results may comprise web links, links to content or applications stored locally on the device, images, videos, or the like.

Regardless of whether the second device stores an application specifically configured to interact with the first device, or whether the second device uses a browser or other context-specific application to display the content, the user may access this content in a number of ways. In some implementations, the second device awakens and directly causes display of the content upon receiving the instruction from the first device (or simply causes display of the content if the second device is already awake). In other instances, the second device may display content associated with the user's voice command (e.g., details regarding Benjamin Franklin) on a "lock screen" of the second device. Thereafter, when the user unlocks the device, the second device may display even more details regarding the subject (e.g., on the application described above, on a webpage regarding Benjamin Franklin, or the like). In another example, the second device may simply display a notification in a notification area or notification tray of the device. For instance, the second device may display a notification alongside notifications displayed when the device receives a text message, email, phone call, voicemail, or the like. The second device may then display all of the visual content upon the user selecting the notification from the notification area.

While the above example describes transitioning from outputting audible content to outputting visual content, the techniques described herein may transition from displaying visual content to outputting audible content, from displaying visual content on a first device to displaying visual content on a second device, or from outputting audible content on a first device to outputting audible content on a second device. In these examples, a user may initiate the transition via a voice command, activation of a physical or soft button, a gesture, via a mouse click, or the like.

In addition, while the above example describes a user transitioning content from one device associated with the user to another device associated with the same user, in other examples the user may transition content to a device associated with another user. For example, a first user may be listening to or viewing an article in a newspaper via a first device. The first user may request, for example via a voice command, to share the article by transitioning the article to a device associated with a second user. The techniques may then provide content or a notification for accessing the content to the device of the second user, which may display or otherwise output the content if the second user so requests.

The devices and techniques described above and below may be implemented in a variety of different architectures and contexts. One non-limiting and illustrative implementation is described below. It is specifically noted that while the techniques are described with reference to a voice-controlled device, these techniques may apply to any other types of client computing device capable of capturing audio.

FIG. 1 shows an illustrative voice interaction computing architecture 100 set in a home environment 102 that includes a user 104. The architecture 100 also includes a voice-controlled device 106 with which the user 104 may interact. In the illustrated implementation, the voice-controlled device 106 is positioned on a table within a room of the home environment 102. In other implementations, the voice-controlled device 106 may be placed or mounted in any number of locations (e.g., ceiling, wall, in a lamp, beneath a table, under a chair, etc.). Further, more than one voice-controlled device 106 may be positioned in a single room, or one device may be used to accommodate user interactions from more than one room.

Generally, the voice-controlled device 106 includes a microphone unit that includes at least one microphone 108 and a speaker unit that includes at least one speaker 110 to facilitate audio interactions with the user 104 and/or other users. In some instances, the voice-controlled device 106 is implemented without a haptic input component (e.g., keyboard, keypad, touch screen, joystick, control buttons, etc.) or a display. In certain implementations, a limited set of one or more haptic input components may be employed (e.g., a dedicated button to initiate a configuration, power on/off, etc.). Nonetheless, the primary and potentially only mode of user interaction with the voice-controlled device 106 may be through voice input and audible output. One example implementation of the voice-controlled device 106 is provided below in more detail with reference to FIG. 8.

The microphone(s) 108 of the voice-controlled device 106 detects audio from the environment 102, such as sounds uttered from the user 104, and generates a representative audio signal. As illustrated, the voice-controlled device 106 includes a processor 112 and memory 114, which stores or otherwise has access to a speech-recognition engine 116. As used herein, a processor may include multiple processors and/or a processor having multiple cores. The speech-recognition engine 116 performs audio recognition on signals generated by the microphone(s) based on sound within the environment 102, such as utterances spoken by the user 104. For instance, the speech-recognition engine 116 may identify both speech (i.e., voice commands) of the user and non-speech commands (e.g., a user clapping, tapping a table, etc.). The voice-controlled device 106 may perform certain actions in response to recognizing this audio, such as speech from the user 104. For instance, the user may speak predefined commands (e.g., "Awake", "Sleep", etc.), or may use a more casual conversation style when interacting with the voice-controlled device 106 (e.g., "I'd like to go to a movie. Please tell me what's playing at the local cinema.").

In some instances, the voice-controlled device 106 may operate in conjunction with or may otherwise utilize computing resources 118 that are remote from the environment 102. For instance, the voice-controlled device 106 may couple to the remote computing resources 118 over a network 120. As illustrated, the remote computing resources 118 may be implemented as one or more servers 122(1), 122(2), . . . , 122(P) and may, in some instances, form a portion of a network-accessible computing platform implemented as a computing infrastructure of processors, storage, software, data access, and so forth that is maintained and accessible via a network such as the Internet. The remote computing resources 118 do not require end-user knowledge of the physical location and configuration of the system that delivers the services. Common expressions associated for these remote computing resources 118 include "on-demand computing", "software as a service (SaaS)", "platform computing", "network-accessible platform", "cloud services", "data centers", and so forth.

The servers 122(1)-(P) include a processor 124 and memory 126, which may store or otherwise have access to some or all of the components described with reference to the memory 114 of the voice-controlled device 106. In some instances the memory 126 has access to and utilizes another speech-recognition engine 128 for receiving audio signals from the device 106, recognizing audio (e.g., speech) and, potentially, causing performance of an action in response. In some examples, the voice-controlled device 106 may upload audio data to the remote computing resources 118 for processing, given that the remote computing resources 118 may have a computational capacity that far exceeds the computational capacity of the voice-controlled device 106. Therefore, the voice-controlled device 106 may utilize the speech-recognition engine 128 at the remote computing resources 118 for performing relatively complex analysis on audio captured from the environment 102. In one example, the speech-recognition engine 116 performs relatively basic audio recognition, such as identifying non-speech commands for the purpose of altering audio output by the device and identifying a predefined voice command that, when recognized, causes the device 106 to provide the audio to the remote computing resources 118. The speech-recognition engine 128 of the remote computing resources 118 may then perform speech recognition on these received audio signals to identify voice commands from the user 104. In some examples, the speech-recognition engine 116 may simply function as a keyword spotter to identify one or more predefined utterances, while the speech-recognition engine 128 may identify words within the speech represented by audio signals generated by the voice-controlled device 106. In these examples, a cost of the voice-controlled device 106 may be lessened, given that the speech-recognition engine 116 is fairly simple and inexpensive to provide on the voice-controlled device 106.

Regardless of whether speech recognition occurs locally or remote from the environment 102, the voice-controlled device 106 may receive vocal input, a user's vocal operational request or command (generally referred to herein as a "command") from the user 104. The voice-controlled device 106 and/or the remote computing resources 118 may perform speech recognition to interpret the command. A command may be presented in any form, such as a question, instruction, statement, sound (hand clapping), code, etc. Essentially, a command may be any type of operation, such as authentication, database inquires, requesting and consuming entertainment (e.g., gaming, finding and playing music, movies or other content, etc.), personal information management (e.g., calendaring, note taking, etc.), online shopping, financial transactions, activating the voice-controlled device 106, notification, and so forth.

The voice-controlled device 106 may communicatively couple to the network 120 via wired technologies (e.g., wires, USB, fiber optic cable, etc.), wireless technologies (e.g., RF, WiFi, cellular, satellite, Bluetooth, etc.), or other connection technologies. The network 120 is representative of any type of communication network, including data and/or voice network, and may be implemented using wired infrastructure (e.g., cable, CAT5, fiber optic cable, etc.), a wireless infrastructure (e.g., RF, WiFi, cellular, microwave, satellite, Bluetooth, etc.), and/or other connection technologies.

As illustrated, the memory 114 of the voice-controlled device 106 stores or otherwise has access to the speech-recognition engine 116, and may also include a media player. The media player may function to output any type of content on any type of output component of the device 106. For instance, the media player may output audio of a video or standalone audio via the speaker(s) 110. For example, the user 104 may provide a command to the voice-controlled device 106 to instruct the media player to cause output of a certain song or other audio file. Conversely, the voice-controlled device 106 may utilize the media player to play audio back to the user 104 when engaging in a back-and-forth interaction with the user 104.

In some instances, and as described above, the voice-controlled device 106 may also interact with other devices within the environment 102, such as illustrated device 130, to supplement the capabilities of the voice-controlled device 106. For instance, the voice-controlled device 106 may utilize its speaker(s) 110 to output audible content and may utilize the displays of other devices in the environment to provide additional content. As illustrated, the memory 114 of the voice-controlled device 106 also stores or has access to a content-transition engine 132. The content-transition engine 132 may function to interact with other devices within the environment, such as the device 130, to instruct the other devices to output additional content. While FIG. 1 illustrates the device 130 as a tablet computing device, it is to be appreciated that these other devices may include laptop computers, mobile phones, desktop computers, televisions, or the like. Each device 130 is communicatively coupled to network 120 via wired technologies (e.g.: wires, USB, fiber optic cable, etc.), wireless technologies (e.g.: RF, WiFi, cellular, satellite, Bluetooth etc.), or other connection technologies. In addition, while the voice-controlled device 106 may utilize these other devices to output visual content, the voice-controlled device 106 may additionally or alternatively utilize these devices to output additional audible content.

In the illustrated example, the user 104 issues the following voice command at 134(1): "Please tell me about Ben Franklin." The microphone 108 of the voice-controlled device 106 may capture this audio and generate a representative audio signal. The voice-controlled device 106 may then either perform speech recognition locally (e.g., using the speech-recognition engine 116) and/or may upload this audio signal to the remote computing resources 118 for performing the speech recognition (e.g., using the speech-recognition engine 128). In either instance, the voice-controlled device 106 may locate or receive content to output to the user 104 in response to decoding the user's vocal utterance/command.

At 134(2), the speaker(s) 110 of the voice-controlled device 106 output the following response: "Benjamin Franklin was one of the founding fathers of the United States of America. Would you like to read additional content on your tablet?" In response, at 134(3), the user 104 utters the following: "Yes, please." The voice-controlled device 106 again generates an audio signal representative of the speech and, after the speech is recognized, the content-transition engine 132 may instruct another device, such as the device 130, to output visual content regarding Benjamin Franklin.

To do so, the voice-controlled device 106, the remote computing resources 118, or another entity may identify display-capable devices that are proximate to the voice-controlled device 106 and/or the user 104. For instance, the voice-controlled device 106 may use any sort of wireless network or protocol to detect the presence of other devices able to communicate wirelessly, such as via WiFi, Bluetooth, RF signals, or the like. The voice-controlled device 106 may identify these devices directly, or may identify devices that are connected to the same wireless access point (WAP) as the voice-controlled device 106. The voice-controlled device 106 may also identify proximate devices in any other manner, such as receiving global positioning (GPS) location data from other devices, by using a camera and performing image recognition techniques, by querying the user as to which devices are in the environment 102, and/or the like.

In addition, the voice-controlled device 106 may identify a device that is not only proximate to the user, but that is also associated with the user. In some instances, the user may register his or her devices with the entity that provides support to the voice-controlled device 106. As such, the voice-controlled device 106 may check this registry to identify which devices are associated with the user 104. Again, the voice-controlled device 106 may alternatively make this determination in any other manner, such as by directly querying the user or the like.

In this example, the voice-controlled device 106 may identify the display-capable device 130 that is associated with the user 104. In response, the content-transition engine 132 may either retrieve content and provide this content to the device 130, may provide an instruction to the device 130 to retrieve particular content, or the remote computing resources 118 may provide the content or the instruction to retrieve the content to the device 130. Generally described, the voice-controlled device 106 may provide information to the display-capable device 130. The provided information may include the instructions, content and/or a location identifier identifying a location from which the content can be obtained.

In response to receiving information from the voice-controlled device 106, as illustrated, the device 130 may receive and/or obtain the relevant content and display that content. Continuing with the above example, the device 130 will receive content related to the user's initial request to learn about "Ben Franklin" and visually display that content to the user 104. As illustrated, the content on the device 130 is more detailed in this example than the summary provided by the audio from the voice-controlled device 106. In one particular example, the audio content output by the voice-controlled device 106 comprises a summary of a content item (e.g., a Wikipedia® article about Benjamin Franklin), while the content output on the display of the device 130 comprises an additional portion or the entire content item (e.g., the entire Wikipedia® article).

As FIG. 1 illustrates, a user is able to provide a voice command to the voice-controlled device 106 and, in response, receive information audibly via the voice-controlled device 106. In addition, the user receives additional visual content from one or more devices that are proximate to the user, thus providing the user with a greater amount of content about the desired subject.

Figure 2:
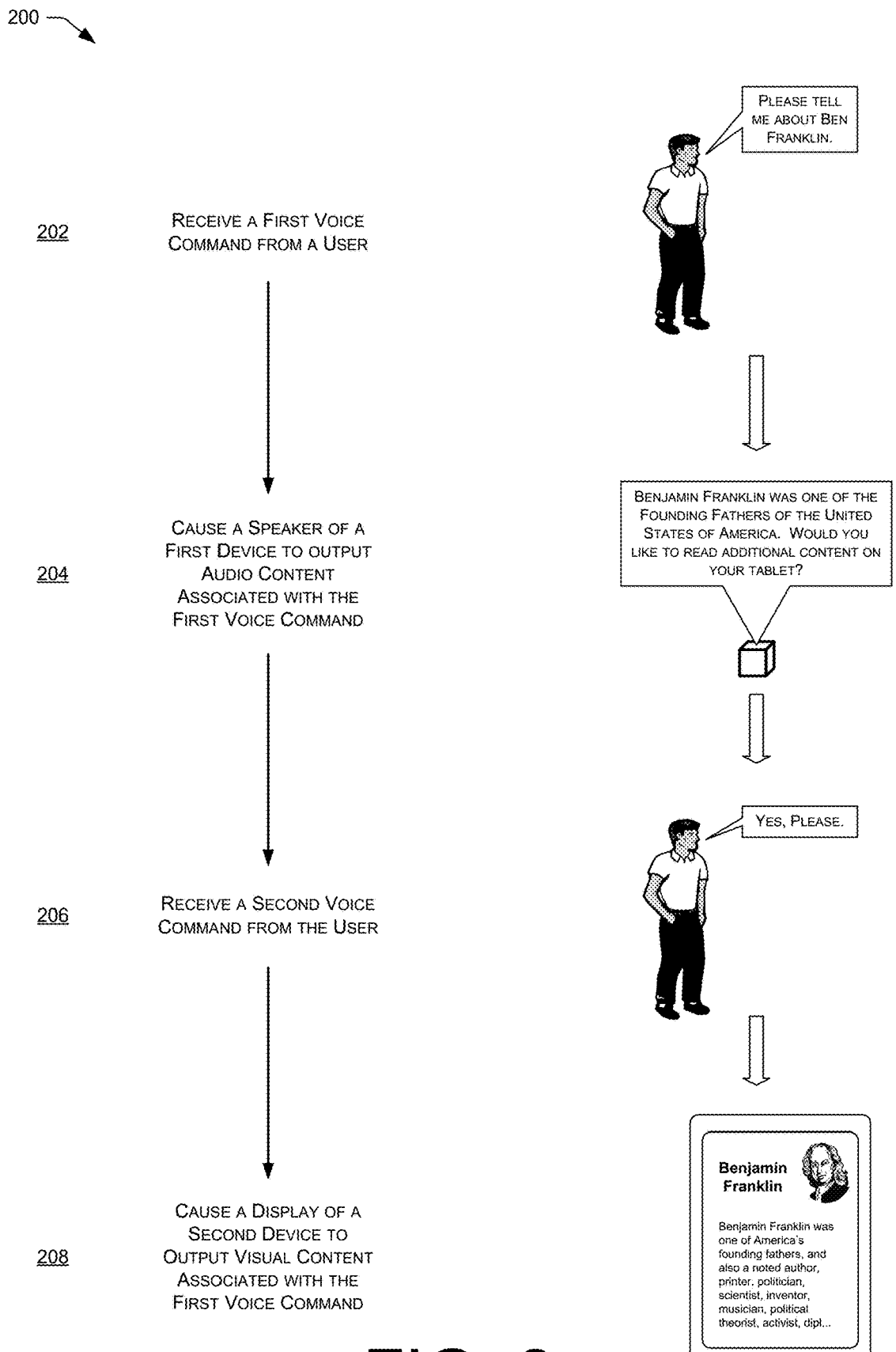
FIG. 2 depicts a flow diagram of an example process for receiving a first voice command, outputting audio content on a first device in response, receiving a second voice command requesting to receive visual content, and outputting visual content on a second device in response to the second voice command, according to various implementations.

FIG. 2 depicts a flow diagram of an example process 200 for receiving a first voice command, outputting audio content on a first device in response, receiving a second voice command requesting to receive visual content, and outputting visual content on a second device in response to the second voice command, in accordance with various implementations. While this process is described as being performed by the voice-controlled device 106 of FIG. 1, it is to be appreciated that the process may be performed in whole or in part by the remote computing resources 118 or one or more other entities.

The process 200 (as well as each process described herein) is illustrated as a logical flow graph, each operation of which represents a sequence of operations that can be implemented in hardware, software, or a combination thereof. In the context of software, the operations represent computer-executable instructions stored on one or more computer-readable media that, when executed by one or more processors, perform the recited operations. Generally, computer-executable instructions include routines, programs, objects, components, data structures, and the like that perform particular functions or implement particular abstract data types.

The computer-readable media may include non-transitory computer-readable storage media, which may include hard drives, floppy diskettes, optical disks, CD-ROMs, DVDs, read-only memories (ROMs), random access memories (RAMs), EPROMs, EEPROMs, flash memory, magnetic or optical cards, solid-state memory devices, or other types of storage media suitable for storing electronic instructions. In addition, in some embodiments the computer-readable media may include a transitory computer-readable signal (in compressed or uncompressed form). Examples of computer-readable signals, whether modulated using a carrier or not, include, but are not limited to, signals that a computer system hosting or running a computer program can be configured to access, including signals downloaded through the Internet or other networks. Finally, the order in which the operations are described is not intended to be construed as a limitation, and any number of the described operations can be combined in any order and/or in parallel to implement the process.

At 202, the voice-controlled device 106 receives a first voice command from the user 104. As described above, the microphone 108 of the voice-controlled device 106 captures the audio and generates a representative audio signal. Thereafter, the voice-controlled device 106, the remote computing resources 118, or another entity may perform speech recognition on the signal to identify the first voice command.

At 204, and in response, the voice-controlled device 106 causes its speakers to output audible content associated with the first voice command. In this example, the speaker outputs content regarding the subject of the first voice command, Benjamin Franklin.

At 206, the voice-controlled device 106 receives a second voice command from the user 104 requesting to output additional content on a display-capable device. In this example, the second voice command is in the form of the user 104 responding positively to a query output by the device 106, while in other examples the user 104 may simply issue this command without a prompt from the device (e.g., while or after the device 106 outputs the audible content at 204).

At 208, the voice-controlled device 106 causes a display of another device to output visual content associated with the first voice command. In this example, this comprises causing a display of a tablet computing device of the user 104 to output visual content regarding Benjamin Franklin.

While FIG. 2 illustrates a first device outputting audible and, thereafter, a second device outputting visual content, in other instances this process may be reversed. For instance, a first device may output visual content, at which point a user may request to transition to the output of audible content on another device. In response, a second device may output audible content. In addition or in the alternative, a first device may output audible content, may receive a request from the user to transition to a second device, and, in response, the second device may also output audible content. Or, the first device may output visual content, may receive a request from the user to transition to the second device, and, in response, the second device may also output visual content.

Figure 3A:
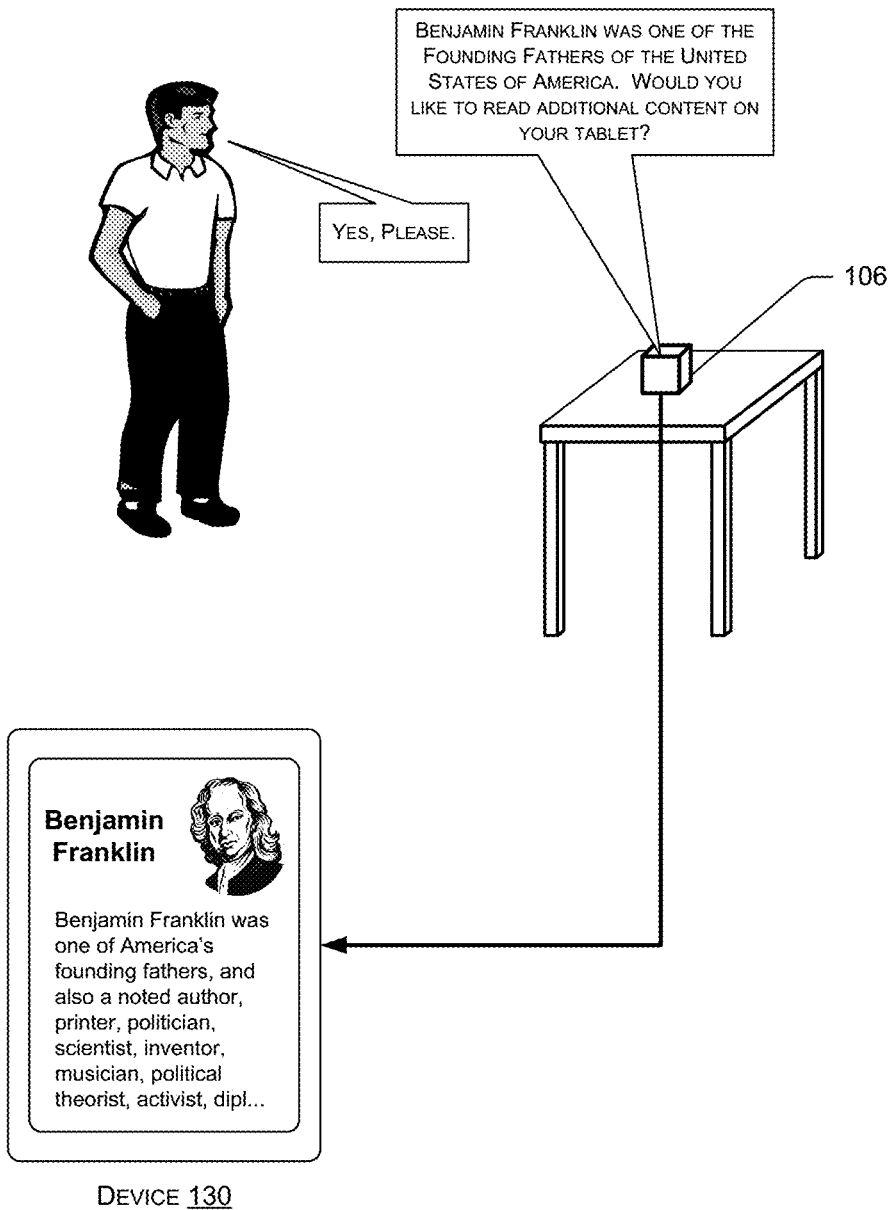
FIGS. 3A-3C depict respective manners in which the voice-controlled device of FIG. 1 may output audio content and instruct another device with display capabilities to output visual content, according to various implementations.
Figure 3B:
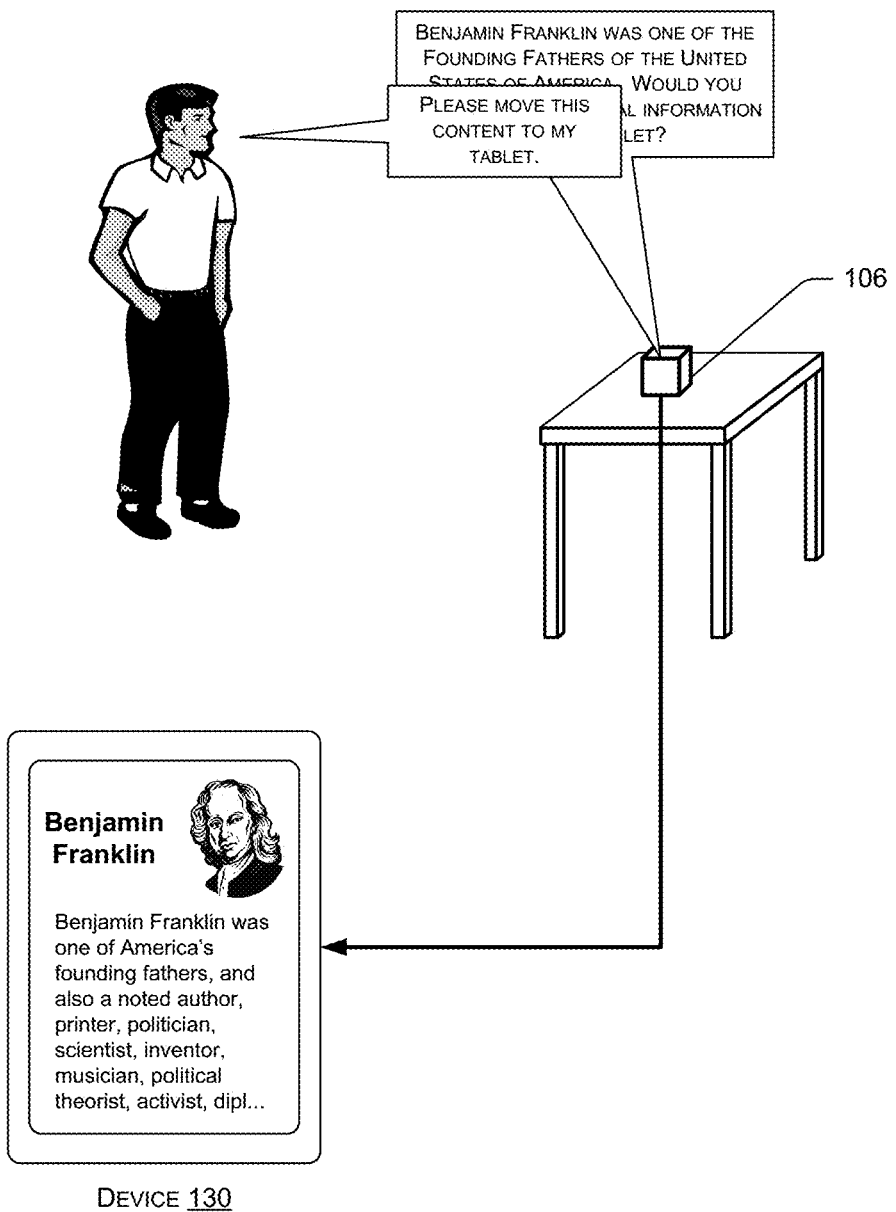
Figure 3C:
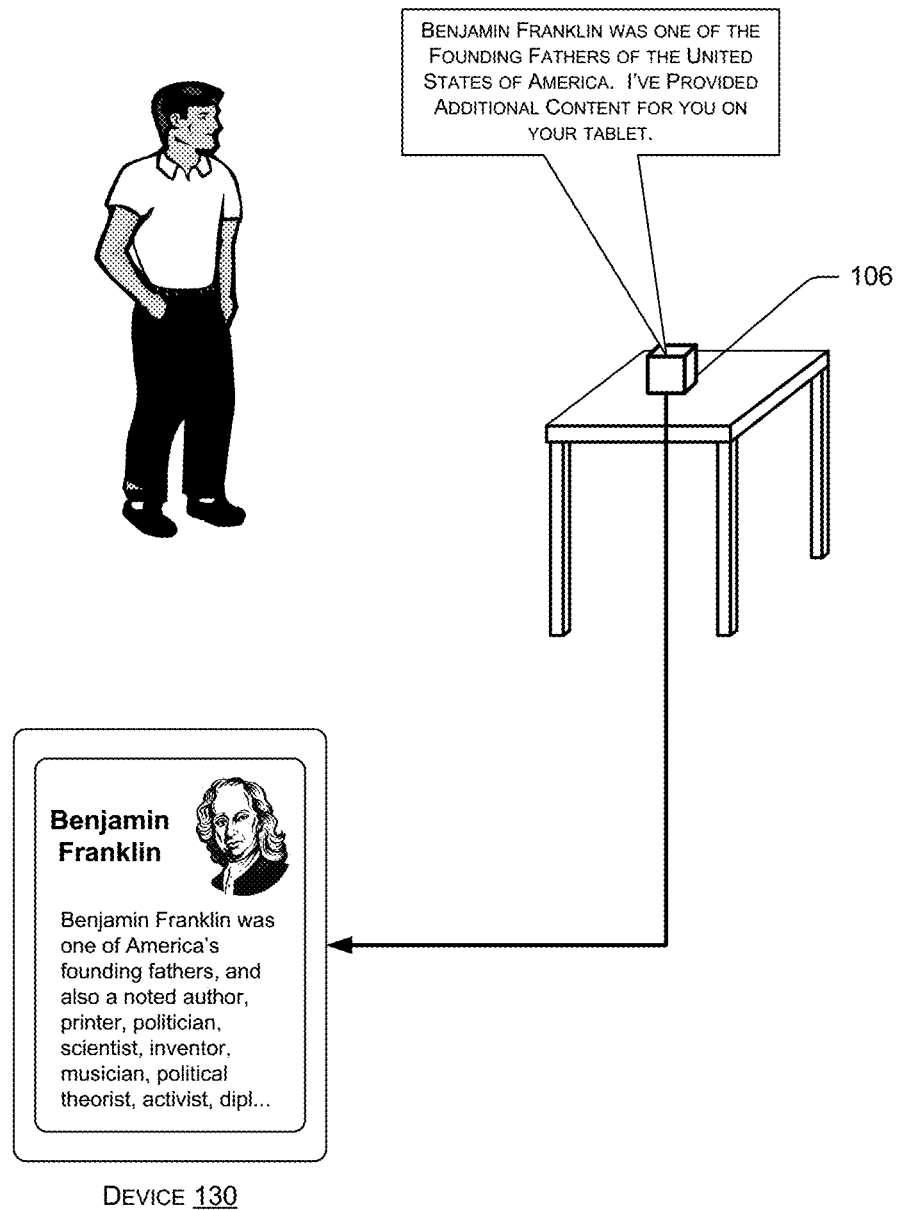

FIGS. 3A-3C depict respective manners in which the voice-controlled device of FIG. 1 may output audio content and instruct another device with display capabilities to output visual content, in accordance with various implementations. FIG. 3A illustrates that the voice-controlled device 106 may first output the audible content regarding Benjamin Franklin discussed above, before outputting a query to the user 104 asking whether the user 104 would like to view additional content regarding Benjamin Franklin on the user's tablet computer. In this example, the user 104 responds that he would and, hence, the voice-controlled device 106 instructs the device 130 to display the additional content.

FIG. 3B, meanwhile, illustrates the user 104 issuing a voice command to the voice-controlled device 106 while the device 106 outputs the audible content discussed above. In this example, the user 104 states the following: "Please move this content to my tablet" while the voice-controlled device 106 is outputting a portion of the audible content. In response to identifying this speech, the voice-controlled device 106 sends information to the device 130 instructing it to display additional content regarding Benjamin Franklin.

FIG. 3C illustrates yet another example. As illustrated, the voice-controlled device 106 outputs the audible content discussed above and, thereafter, informs the user that the device 106 has provided additional content on the user's tablet (i.e., the device 130). As such, the user 104 receives additional content regarding the desired subject without issuing a voice command subsequent to the initial voice command requesting information about Benjamin Franklin.

Figure 4:
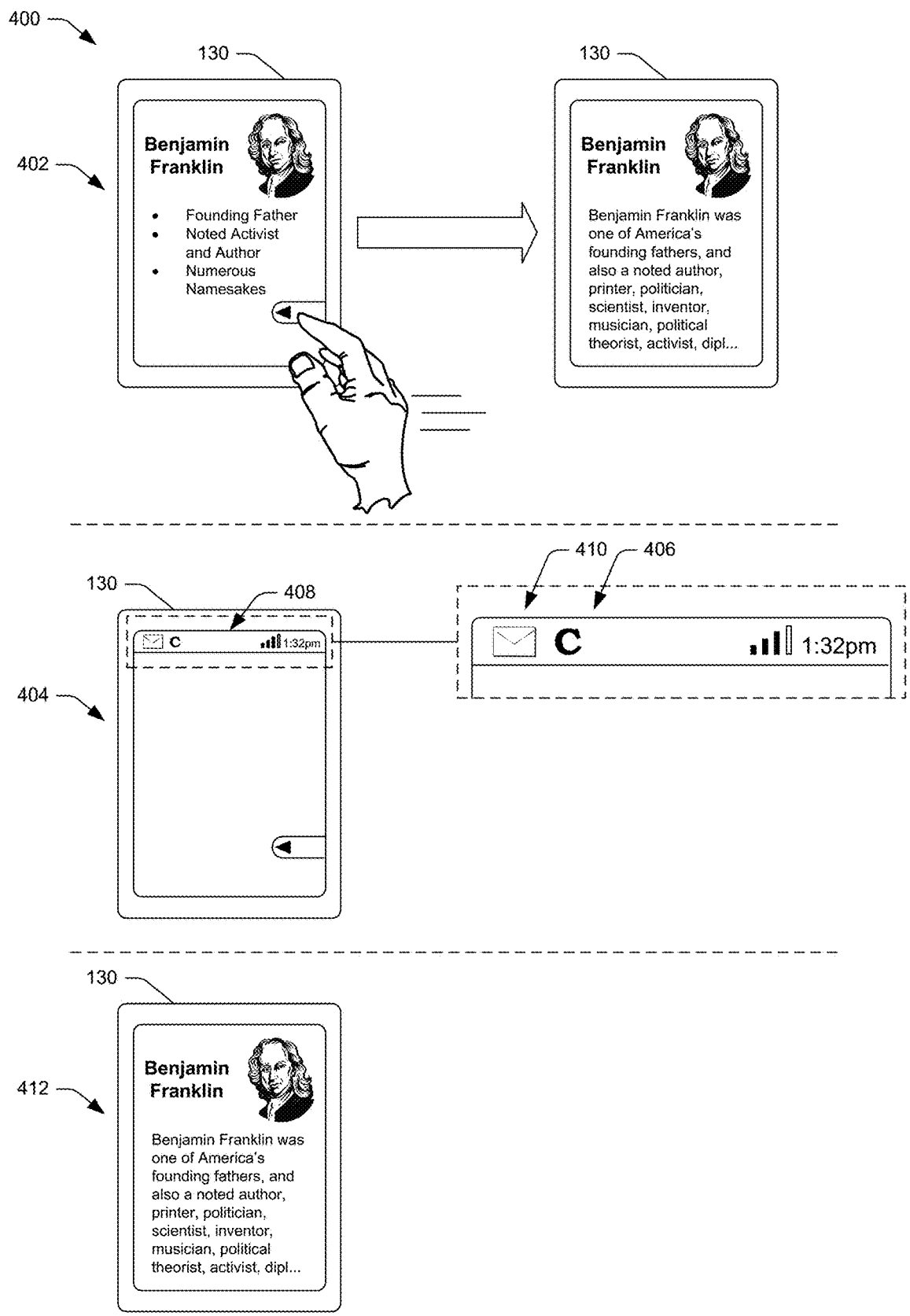
FIG. 4 illustrates three example ways that the device with display capabilities may indicate to the user of FIGS. 3A-3C that the device has visual content for viewing by the user, according to various implementations.

FIG. 4 illustrates three example scenarios 400 where the device 130 with display capabilities indicates to the user 104 that the device has visual content for viewing by the user 104. As illustrated, a first scenario 402 shows that the device 130 is in a locked state and displays initial content on a "lock screen" of the device 130 after receiving an indication from the voice-controlled device 106 (or the remote computing resources 118) to display content regarding Benjamin Franklin. As illustrated, the device 130 shows a first, initial amount of content on the lock screen while the device 130 is in a locked state and then displays a second, greater amount of content on the display once the user unlocks the device 130.

A second scenario 404, meanwhile, illustrates that the device 130 may simply display initial content in the form of a notification 406 in a notification area 408 of the display. That is, in response to receiving an indication that a user would like to receive additional information regarding an interaction initiated via the voice-controlled device 106, the device 130 may display a notification 406 identifying that additional content is available to the user. This notification may be similar to a notification 410 for a received text message, a notification for a received email, or the like. In response to the user 104 selecting the notification 406, the device 130 may display the additional content (e.g., regarding Benjamin Franklin). In this example, the notification 406 comprises a "C" to illustrate that the device will display content, such as a Wikipedia® article on Benjamin Franklin, in response to a receiving a selection from the user 104 of the notification 406. Of course, while FIG. 4 illustrates one example, it is to be appreciated that the notification may be of any other form or illustration.

Finally, a third scenario 412 illustrates the scenario described above with reference to FIGS. 1-3C, where the device 130 directly displays content regarding the desired subject. As described above, the voice-controlled device 106 may, in some instances, provide information that awakens the device 130 and instructs the device to display the content. Awakening the device 130 may include causing the device 130 to transition from a state in which the display is off to a state in which the display is on (to display the content). Of course, awakening the device 130 may, in other implementations, cause the device 130 to transition from one state, such as a locked state, to any other state.

Figure 5:
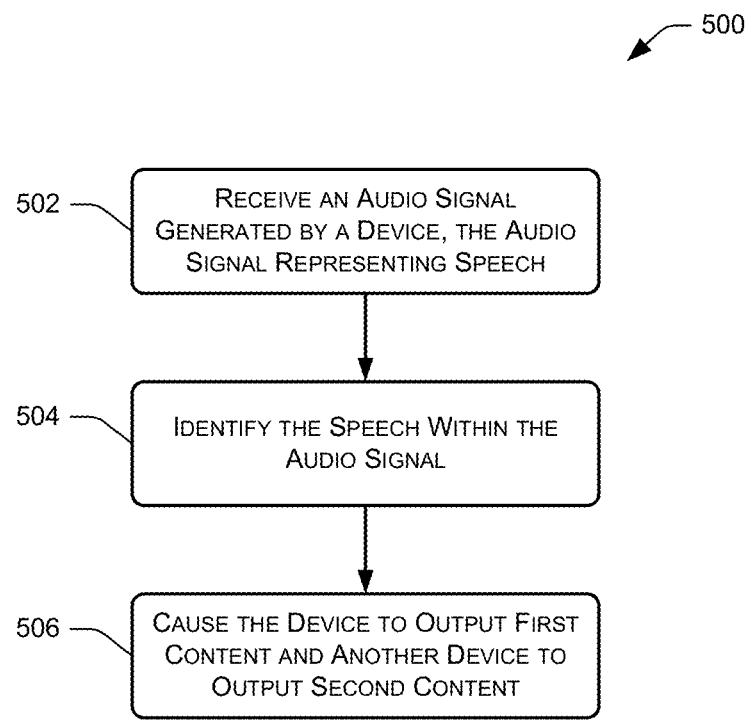
FIG. 5 depicts a flow diagram of an example process for receiving an audio signal, identifying speech therein, and, in response, causing a first device to output first content and a second device to output second content, according to various implementations.

FIG. 5 depicts a flow diagram of an example process 500 that may be implemented using the techniques described above. At 502, the process 500 receives an audio signal generated by a device, with the audio signal representative of speech from a user. At 504, the process identifies the speech within the audio signal. In some instances, the speech includes a user command requesting or issuing a query regarding certain content. At 506, and in response to identifying the speech, the process 500 causes the voice-controlled device 106 to output first content associated with the voice command and causes another device 130 to output second, additional content associated with the voice command. In some instances, the first content comprises audible content while the second content comprises visual content.

Figure 6:
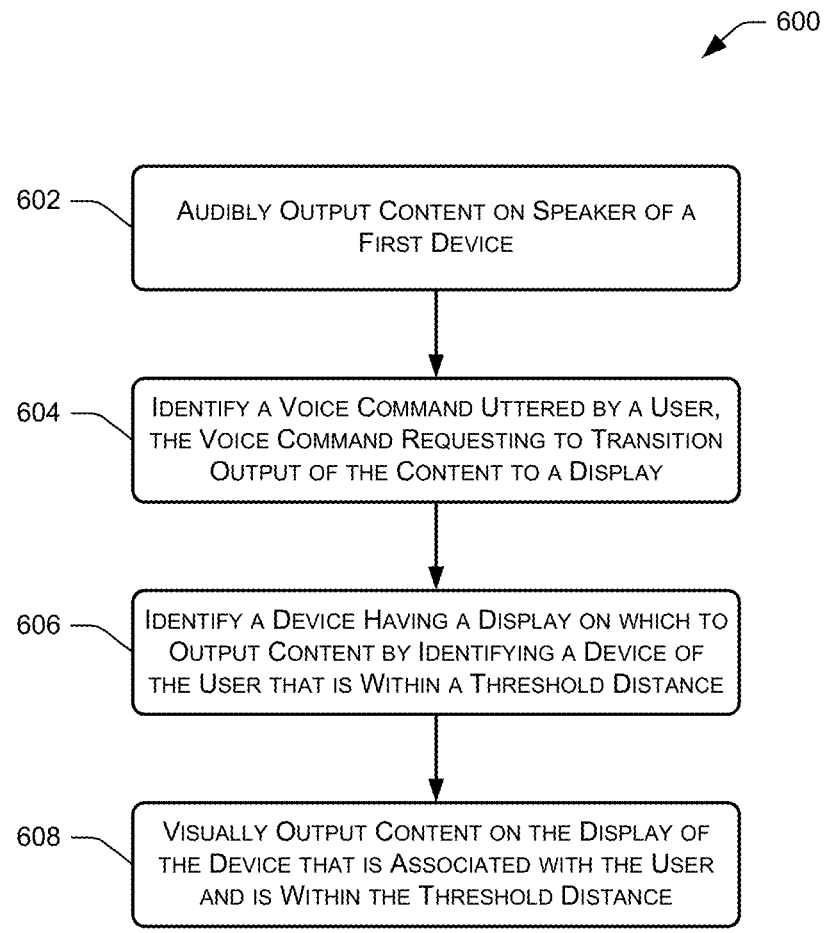
FIG. 6 depicts a flow diagram of an example process for audibly outputting content on a first device and visually outputting content on a second device in response to identifying a voice command requesting to transition the output of content to a device that includes display capabilities, according to various implementations.

FIG. 6 depicts a flow diagram of another example process 600. At 602, the process 600 audibly outputs content on a speaker of a first device. At 604, the process 600 identifies a voice command uttered by a user, the voice command requesting to transition output of the content to a display for visual presentation. At 606, the process 600 identifies a device on which to output the content by identifying a device that is within a threshold distance of the first device and/or the user. In other instances, the process 600 identifies and selects a device on which to output content based on a type of the device, information regarding whether the device is powered on, and the like. The process 600 may also ensure that this other device is associated with the user. At 608, the process 600 visually presents the content on the identified device that is within the threshold distance.

Figure 7:
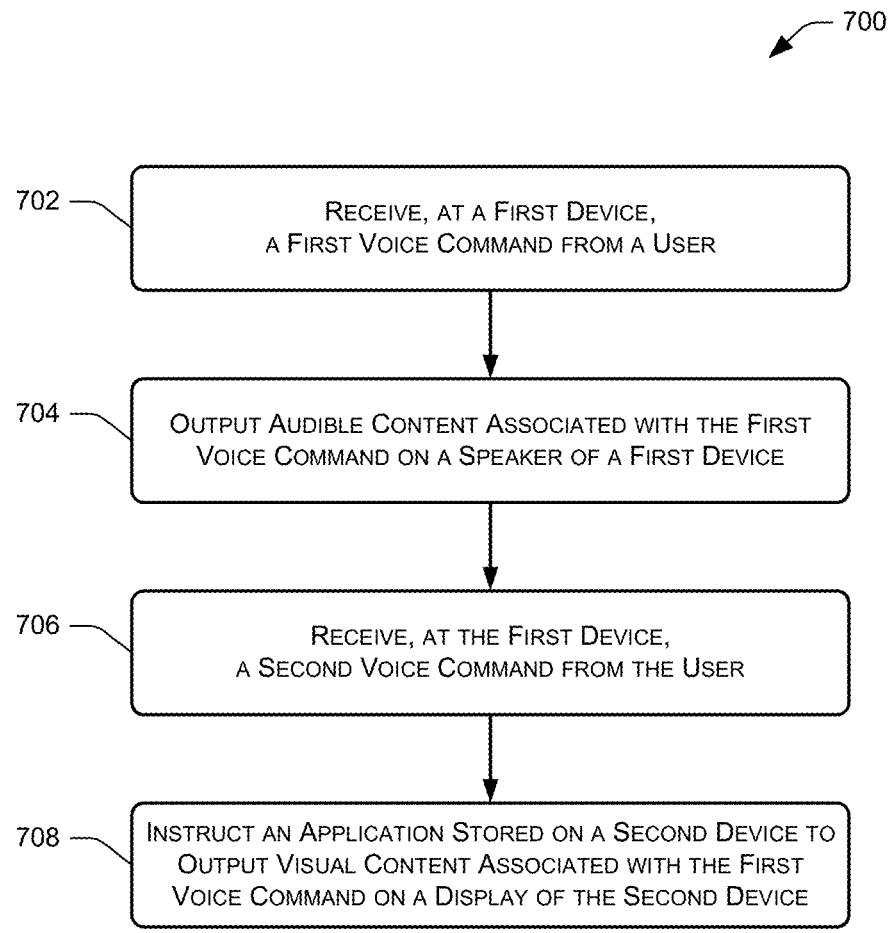
FIG. 7 depicts a flow diagram of an example process for receiving a voice command at a first device, outputting audible content at the first device, receiving a second voice command at the first device, and, in response, instructing an application stored on a second device to display visual content associated with the first voice command, according to various implementations.

FIG. 7 depicts a flow diagram of an example process 700. At 702, the process 700 receives, at a first device, a first voice command from a user. At 704, and in response, the process 700 outputs audible content associated with the first voice command on a speaker of the first device. At 706, the process 700 receives, at the first device, a second voice command from the user. At 708, and in response, the process 700 provides information to an application stored on a second device that includes instructions to output visual content associated with the first voice command on a display of the second device. The information may also include the additional content to be presented. Optionally, the information may include an identifier and/or link to a location from which the content can be obtained by the second device. As described above, the application may comprise a "companion application" that is specifically configured to communicate with the voice-controlled device 106. For instance, the application may both receive content from and provide content to the voice-controlled device.

Figure 8:
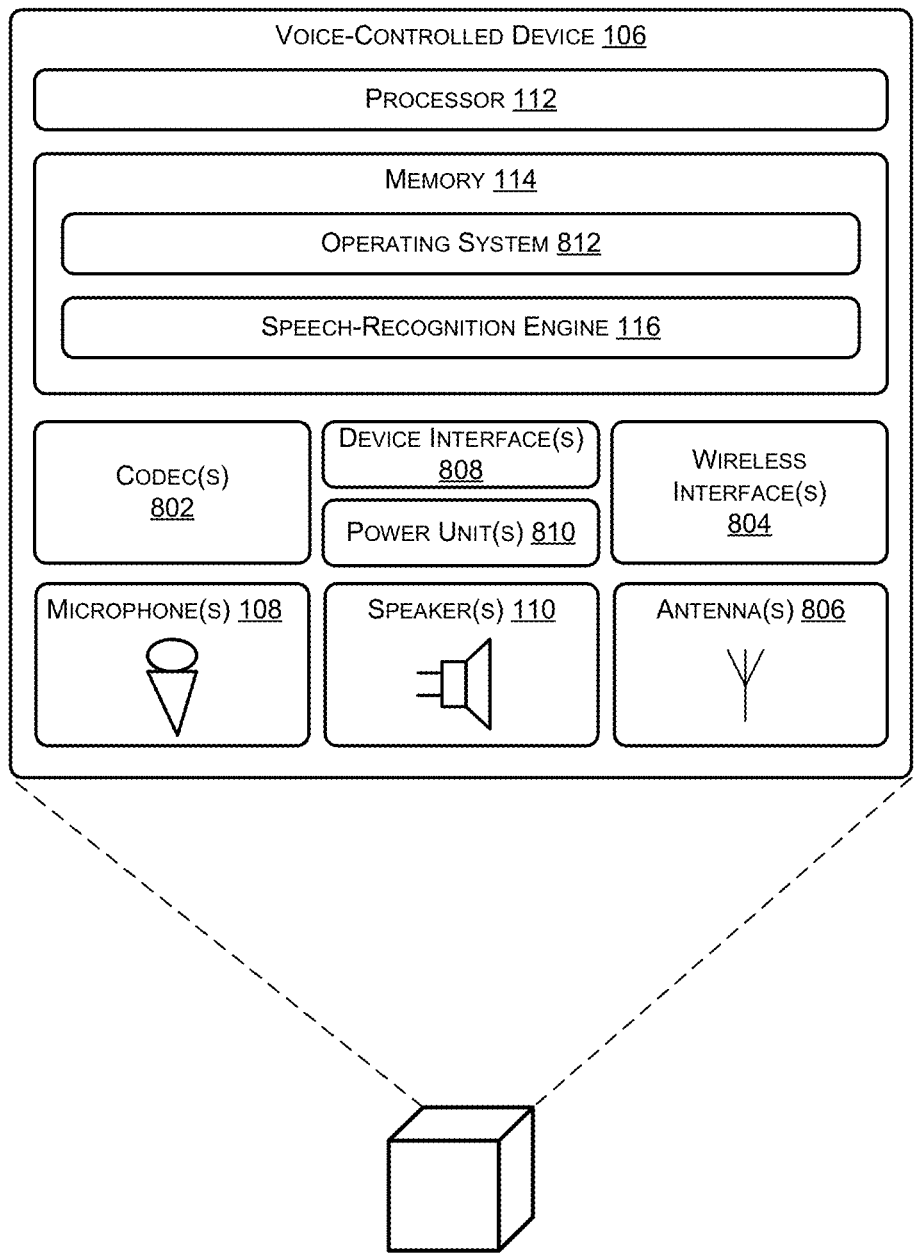
FIG. 8 shows a block diagram of selected functional components implemented in the voice-controlled device of FIG. 1, according to various implementations.

FIG. 8 shows a block diagram of selected functional components implemented in the voice-controlled device 106 of FIG. 1. Generally, the voice-controlled device 106 may be implemented as a standalone device that is relatively simple in terms of functional capabilities with limited input/output components, memory and processing capabilities. For instance, the voice-controlled device 106 does not have a keyboard, keypad, or other form of mechanical input in some implementations, nor does it have a display or touch screen to facilitate visual presentation and user touch input. Instead, the voice-controlled device 106 may be implemented with the ability to receive and output audio, a network interface (wireless or wire-based), power, and limited processing/memory capabilities.

In the illustrated implementation, the voice-controlled device 106 includes the processor 112 and memory 114. The memory 114 may include computer-readable storage media ("CRSM"), which may be any available physical media accessible by the processor 112 to execute instructions stored on the memory. In one basic implementation, CRSM may include random access memory ("RAM") and Flash memory. In other implementations, CRSM may include, but is not limited to, read-only memory ("ROM"), electrically erasable programmable read-only memory ("EEPROM"), or any other medium which can be used to store the desired information and which can be accessed by the processor 112.

The voice-controlled device 106 includes a microphone unit that comprises one or more microphones 108 to receive audio input, such as user voice input. The voice-controlled device 106 also includes a speaker unit that includes one or more speakers 110 to output audio sounds. One or more codecs 802 are coupled to the microphone(s) 108 and the speaker(s) 110 to encode and/or decode the audio signals. The codec may convert audio data between analog and digital formats. A user may interact with the device 106 by speaking to it, and the microphone(s) 108 captures sound and generates an audio signal that includes the user speech. The codec 802 encodes the user speech and transfers that audio data to other components. The voice-controlled device 106 can communicate back to the user by emitting audible statements through the speaker(s) 110. In this manner, the user interacts with the voice-controlled device 106 simply through speech, without use of a keyboard or display common to other types of devices.

In addition, in some instances users may interact with the voice-controlled device 106 using a device other than the voice-controlled device 106. For instance, a user may utilize the companion application, discussed above, through which the user may provide requests to and receive responses from the voice-controlled device 106. In one particular example, the companion application is a web-based application that is executable on any client computing device. As described above, the companion application may receive requests to display content from the voice-controlled device 106 and may display the appropriate content in response. This may include web links, links to local applications, images, videos, and/or any other type of visual content.

In the illustrated example, the voice-controlled device 106 includes one or more wireless interfaces 804 coupled to one or more antennas 806 to facilitate a wireless connection to a network. The wireless interface 804 may implement one or more of various wireless technologies, such as WiFi, Bluetooth, RF, and so on.

One or more device interfaces 808 (e.g., USB, broadband connection, etc.) may further be provided as part of the voice-controlled device 106 to facilitate a wired connection to a network, or a plug-in network device that communicates with other wireless networks. One or more power units 810 are further provided to distribute power to the various components on the voice-controlled device 106.

The voice-controlled device 106 is designed to support audio interactions with the user, in the form of receiving voice commands (e.g., words, phrase, sentences, etc.) from the user and outputting audible feedback to the user. Accordingly, in the illustrated implementation, there are no or few haptic input devices, such as navigation buttons, keypads, joysticks, keyboards, touch screens, and the like. Further there is no display for text or graphical output. In one implementation, the voice-controlled device 106 may include non-input control mechanisms, such as basic volume control button(s) for increasing/decreasing volume, as well as power and reset buttons. There may also be one or more simple light elements (e.g., LEDs around perimeter of a top portion of the device) to indicate a state such as, for example, when power is on or to indicate when a command is received. But, otherwise, the voice-controlled device 106 does not use or need to use any input devices or displays in some instances.

Several modules such as instruction, datastores, and so forth may be stored within the memory 114 and configured to execute on the processor 112. An operating system module 812 is configured to manage hardware and services (e.g., wireless unit, Codec, etc.) within and coupled to the voice-controlled device 106 for the benefit of other modules.

In addition, the memory 114 may include the speech-recognition engine 116, along with one or more other applications, such as a media player and the like. In some instances, some or all of these engines, data stores, and components may reside additionally or alternatively at the remote computing resources 118.

Although the subject matter has been described in language specific to structural features, it is to be understood that the subject matter defined in the appended claims is not necessarily limited to the specific features described. Rather, the specific features are disclosed as illustrative forms of implementing the claims.

What is claimed is:

1. A system comprising:
one or more processors;
memory; and
computer-executable instructions stored in the memory that, when executed by the one or more processors, causes the one or more processors to perform acts comprising:
receiving input audio data from a first device;
performing speech recognition on the input audio data to determine a command to present content via a second device;
transmitting, based at least in part on the command, output audio data to the first device, the output audio data comprising computer-generated speech associated with presenting the content at the second device; and
transmitting data to present the content via the second device, wherein the first device and the second device are associated.

2. The system as recited in claim 1, wherein the output audio data indicates that the content is to be presented at the second device.

3. The system as recited in claim 1, wherein the acts further comprise:
 determining that the input audio data includes a query; and
 performing a search for data based at least in part on the query.

4. The system as recited in claim 1, wherein the acts further comprise:
 determining that the second device is associated with a display; and
 determining that the second device is within a threshold distance of the first device.

5. The system as recited in claim 1, wherein the output audio data includes a query regarding whether the content is to be presented on the second device.

6. The system as recited in claim 1, wherein the input audio data is first input audio data, and wherein the acts further comprise:
 receiving, from the first device, second input audio data including a confirmation to present the content on the second device.

7. The system as recited in claim 1, wherein the input audio data includes a query, wherein the acts further comprise:
 transmitting, based at least in part on the query, a first portion of a query result to the first device; and
 transmitting, based at least in part on the query, a second portion of the query result to the second device.

8. The system as recited in claim 1, wherein the first device and the second device are associated via a registry.

9. A processor-implemented method comprising:
 receiving input audio data from a first device;
 performing speech recognition on the input audio data to determine a command to present content via a second device;
 transmitting, based at least in part on the command, output audio data to the first device, the output audio data comprising computer-generated speech indicating that the content is to be presented at the second device; and
 transmitting data to present the content via the second device, wherein the first device and the second device are associated.

10. The processor-implemented method as recited in claim 9, further comprising:
 determining that the input audio data includes a query; and
 performing a search for data based at least in part on the query.

11. The processor-implemented method as recited in claim 9, further comprising:
 determining that the second device is associated with a display; and
 determining that the second device is within a threshold distance of the first device.

12. The processor-implemented method as recited in claim 9, wherein the output audio data includes a query regarding whether the content is to be presented on the second device.

13. The processor-implemented method as recited in claim 9, wherein the input audio data is first input audio data, the processor-implemented method further comprising:
 receiving, from the first device, second input audio data including a confirmation to present the content on the second device.

14. The processor-implemented method as recited in claim 9, wherein the input audio data includes a query, the processor-implemented method further comprising:
 transmitting, based at least in part on the query, a first portion of a query result to the first device; and
 transmitting, based at least in part on the query, a second portion of the query result to the second device.

15. The processor-implemented method as recited in claim 9, wherein the first device and the second device are associated via a registry.

16. The processor-implemented method as recited in claim 9, wherein the speech identifies the second device.

17. A system comprising:
 one or more processors;
 a memory; and
 computer-executable instructions stored in the memory that, when executed by the one or more processors, causes the one or more processors to perform acts comprising:
  receiving input audio data from a first device;
  performing speech recognition on the input audio data to determine that the input audio data represents a command to present content via a second device;
  transmitting, based at least in part on the command, output audio data to the first device, the output audio data comprising computer-generated speech associated with presenting the content at the second device;
  determining an address associated with the second device; and
  transmitting data to the address to present the content via the second device, wherein the first device and the second device are associated.

18. The system as recited in claim 17, the acts further comprising:
 receiving a command from the first device to register the first device and the second device via a registry.

19. The system as recited in claim 17, wherein the data comprises the content to be presented via the second device.

20. The system as recited in claim 17, wherein the data comprises an instruction to the second device to retrieve the content via a remote computing resource.

* * * * *